United States Patent [19]

Amakasu

[11] Patent Number: 5,359,747
[45] Date of Patent: Nov. 1, 1994

[54] POWER TOOTHBRUSH

[75] Inventor: Mikio Amakasu, Tokyo, Japan

[73] Assignee: Seikosha Co., Ltd., Tokyo, Japan

[21] Appl. No.: 110,606

[22] Filed: Aug. 23, 1993

[30] Foreign Application Priority Data

Aug. 31, 1992 [JP] Japan .................. 4-231968
Feb. 24, 1993 [JP] Japan .................. 5-35301

[51] Int. Cl.$^5$ .................. A61C 17/34; A46B 13/02
[52] U.S. Cl. .................. 15/22.1
[58] Field of Search .................. 15/22.1, 22.2, 22.4

[56] References Cited

U.S. PATENT DOCUMENTS

| | | | |
|---|---|---|---|
| 3,661,018 | 5/1972 | Keefer et al. | 15/22.1 |
| 3,978,852 | 9/1976 | Annoni | 15/22.1 |
| 4,603,448 | 8/1986 | Middleton et al. | 15/22.1 |
| 5,177,826 | 1/1993 | Vrignaud et al. | 15/22.1 |
| 5,226,206 | 7/1993 | Davidovitz et al. | 15/22.1 |
| 5,274,870 | 1/1994 | Stollman | 15/22.1 |

FOREIGN PATENT DOCUMENTS

| | | |
|---|---|---|
| 352864 | 10/1979 | Austria . |
| 500517 | 2/1939 | United Kingdom . |
| 9310721 | 6/1993 | WIPO . |

*Primary Examiner*—Edward L. Roberts
*Attorney, Agent, or Firm*—Jordan and Hamburg

[57] ABSTRACT

A power toothbrush has a superior brushing effect achieved by a brush member which is given a reciprocal motion in the axial direction while at the same time the brush member itself is given a rotary motion and which has a simple construction and is of low cost. A drive shaft is mounted in a casing in such a way that it is free to move in the axial direction. The rotation of a drive motor mounted inside the casing is converted into a reciprocating motion and transmitted to the drive shaft by a first transmission mechanism. A rotary brush member is rotatably mounted on the end of an attachment connected to the drive shaft, and the reciprocating motion, in the axial direction, of the attachment is converted into a rotary motion and transmitted to the rotary brush member by a second transmission mechanism.

11 Claims, 5 Drawing Sheets

POWER TOOTHBRUSH

FIELD OF USE

This invention relates to an electric power toothbrush.

BACKGROUND OF THE INVENTION

Many power toothbrushes have been proposed in the past, and a wide variety of power toothbrushes have been put on sale. Representative examples of these include types in which an attachment with a brush member on the end is fitted to a case in such a way that the attachment is free to move relative to the case and is also removable, and this attachment is driven by a motor mounted inside the case such that the attachment moves in the direction of its length, and types in which the brush member itself is driven instead of the attachment.

For example, in Japanese Patent Publication No. JP 55963/1986, there is disclosed a power toothbrush in which the brush head vibrates finely. In Japanese Patent Publication No. JP 64204/1986, there is disclosed a power toothbrush in which a toothbrush fitted to a drive shaft is driven so that it moves reciprocally either in its axial direction or perpendicular to its axial direction. In Japanese Patent Publication No. JP 79410/1986, there is disclosed a power toothbrush in which the stroke of the axial reciprocating motion of the toothbrush can be changed.

In the conventional types of power toothbrush mentioned above, in power toothbrushes in which the toothbrush is made to vibrate finely, in case the whole toothbrush is gripped firmly, the fine vibration is absorbed and the actual movement of the brush member becomes almost zero, and consequently the brushing effect is poor. In power toothbrushes in which the brush member is mounted on an attachment part (corresponding to the shape of a normal toothbrush) and the attachment part is caused to move, the brush member itself is fixed to the attachment and does not move relative to it. In the types in which the brush member itself rotates, the attachment part on which the brush member is mounted does not move.

An object of the present invention is to provide a power toothbrush having a superior brushing effect, achieved by an attachment on which a brush member is mounted, which is given a reciprocal motion in the axial direction while at the same time the brush member itself is given a rotary motion, and which has a simple construction and is of low cost.

SUMMARY OF THE INVENTION

In this invention a drive shaft is mounted inside a case in such a way that it is free to move in the direction of its axis; the rotation of a drive motor mounted inside this case is converted into a reciprocating motion and transmitted to the drive shaft by a first transmission mechanism; a rotary brush member is rotatably mounted on the end of an attachment connected to this drive shaft; and the axial reciprocal motion of the attachment is converted into a rotary motion and transmitted to the rotary brush member by a second transmission mechanism.

Also, preferably, an extending bar, which is connected to the above-mentioned fixed shaft when the attachment is connected to the drive shaft, is mounted inside the attachment in such a way that the extending bar is free to move relative to the attachment, and a rack which meshes with a pinion provided on the shaft of the rotary brush member is provided on this extending bar, and this rack and pinion make up the second transmission mechanism.

Preferably, the fixed shaft coaxially passes through the drive shaft.

The rotation of the drive motor mounted inside the case is converted and transmitted through the drive shaft to the attachment by the first transmission mechanism, and as this attachment reciprocates the reciprocating motion of the attachment itself is converted and transmitted to the rotary brush member at the end of the attachment by the second transmission mechanism, and this rotary brush member rotates.

DESCRIPTION OF THE PREFERRED EMBODIMENT

Figure 1:
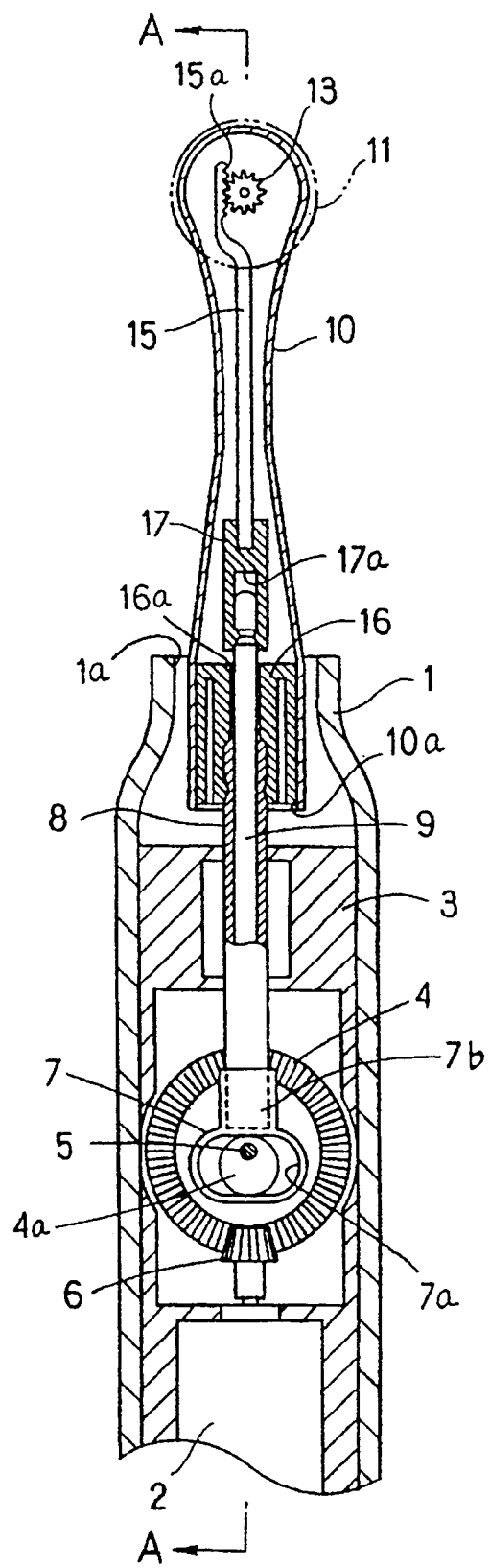
FIG. 1 is a cross-sectional front elevation view of a first preferred embodiment of the invention.
Figure 2:
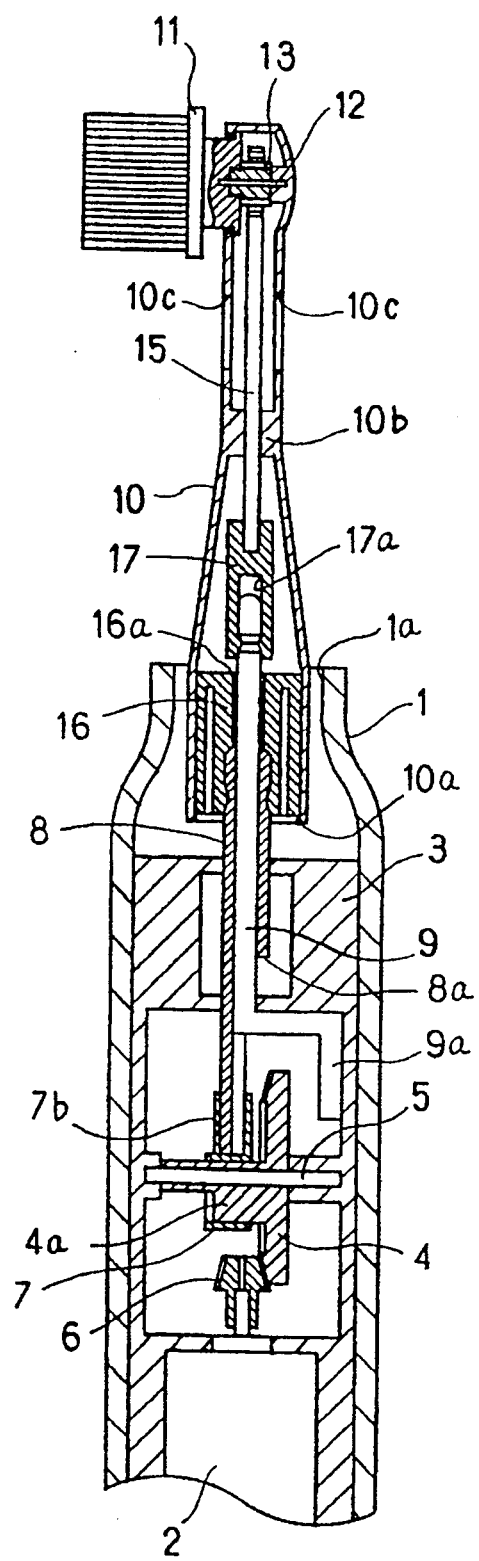
FIG. 2 is a cross-sectional view taken along the line A—A in FIG. 1.

A shown in FIGS. 1 and 2, a direct current motor 2, of which the power supply is a dry cell battery not shown in the drawings, is mounted on a supporting member 3 inside a hollow cylindrical case 1 which has an opening 1a in its top end. A bevel gear 4 is rotatably mounted on the supporting member 3 through a shaft 5, and the teeth of this bevel gear 4 mesh with a motor pinion 6 mounted on the direct current motor 2. An eccentric cam 4a is formed integrally with the bevel gear 4 on the face of the bevel gear 4, and a cam follower 7 engages with this eccentric cam 4a. The cam follower 7, as shown in FIG. 1, has an opening 7a which is of a height equal to the diameter of the eccentric cam 4a, and the eccentric cam 4a fits inside this opening 7a. The unidirectional rotation of the bevel gear 4 about the shaft 5 as center is converted into an up-and-down reciprocal motion by the cam follower 7 following the eccentric cam 4a as it rotates. The eccentric cam 4a and the cam follower 7 make up a first transmission mechanism which converts the rotation of the direct current motor 2 into a reciprocating motion.

A drive shaft 8 of hollow cylindrical form is centrally mounted on the upper part of the supporting member 3 in such a way that it is free to slide in its axial direction (the vertical direction in FIG. 1). The bottom end of the drive shaft 8 is connected to an arm portion 7b that is the upper part of the cam follower 7, so that the up-and-down reciprocating motion of the cam follower 7 is transmitted to the draft shaft 8.

A fixed shaft 9 coaxially passes through the hollow core of the drive shaft 8, the bottom end of this fixed shaft 9 bends in an L-shape and projects out from a cut off portion 8a provided in the drive shaft 8, and this projecting portion 9a is fixed to the inner wall of the supporting member 3.

Water entering through the opening 1a in the top end of the case 1 is prevented by the supporting member 3 from entering as far as the inner part of the case 1 in which the direct current motor 2 and the bevel gear 4, etc., are mounted.

An attachment 10 with an opening 10a in its bottom end is removably attached to the top end of the drive shaft 8 through an adaptor 16 which will be discussed hereinafter. Thus this attachment 10 moves together as one body with the drive shaft 8, reciprocally up-and-down, relative to the case 1.

A shaft 12 is mounted inside the top end of the attachment 10. A rotary brush member 11 having multiple bristles is rotatably and removably mounted on this shaft 12. A pinion 13 is mounted on the shaft 12, which is the center of rotation of the rotary brush, so that the pinion 13 rotates as one body with the rotary brush member 11.

A plurality of protrusions 10b are provided on the inside of the attachment 10. An extending bar 15 is supported by these protrusions 10b inside the attachment 10 in such a way that the extending bar 15 is free to slide in the axial direction (the vertical direction in FIG. 1). The top end of the extending bar 15 is bent into an L-shape, and a rack 15a which meshes with the pinion 13 is formed on this L-shaped part.

The outer face of the attachment 10 is provided with drain holes 10c for draining away any water that enters through the gap between the attachment 10 and the rotary brush member 11.

Figure 4:
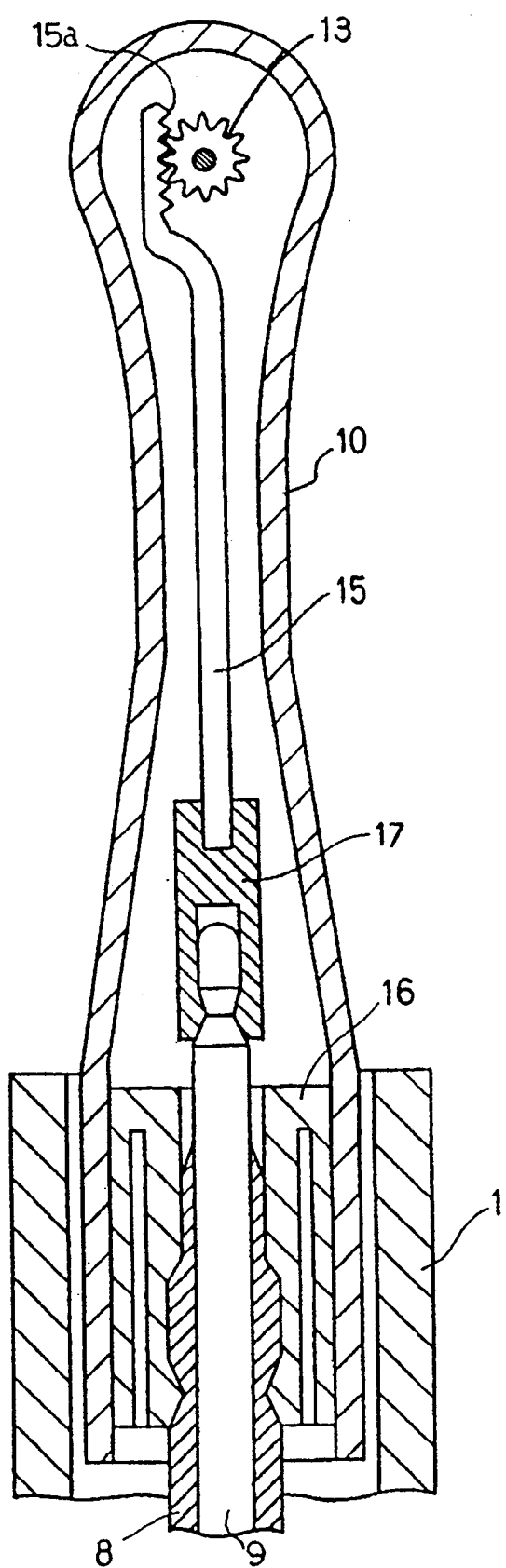
FIG. 4 is an enlarged partial cross-sectional view of the main parts of the embodiment of FIG. 1.

An adaptor 16, which has a through hole 16a in its center, is fixed in the bottom part of the attachment 10. The bottom end of the through hole 16a of the adaptor 16 connects as shown in FIG. 4 with the top end of the drive shaft 8 when the attachment 10 is inserted into the opening 1a in the top of the case 1. Thus the attachment 10 moves as one body with the drive shaft 8, reciprocally up-and-down, relative to the case 1. When the adaptor 16 is fitted like this onto the drive shaft 8, the top end of the fixed shaft 9, which passes through the drive shaft 8, passes through the through hole 16a in the adaptor 16 and projects from the top of the adaptor 16 into the inside of the attachment 10. A coupler 17, which has an opening 17a in its bottom end, is fixed to the bottom end of the extending bar 15. The opening 17a in this coupler 17 connects with the top end of the fixed shaft 9 when the adaptor 16 of the attachment 10 is fitted onto the draft shaft 8.

Figure 3:
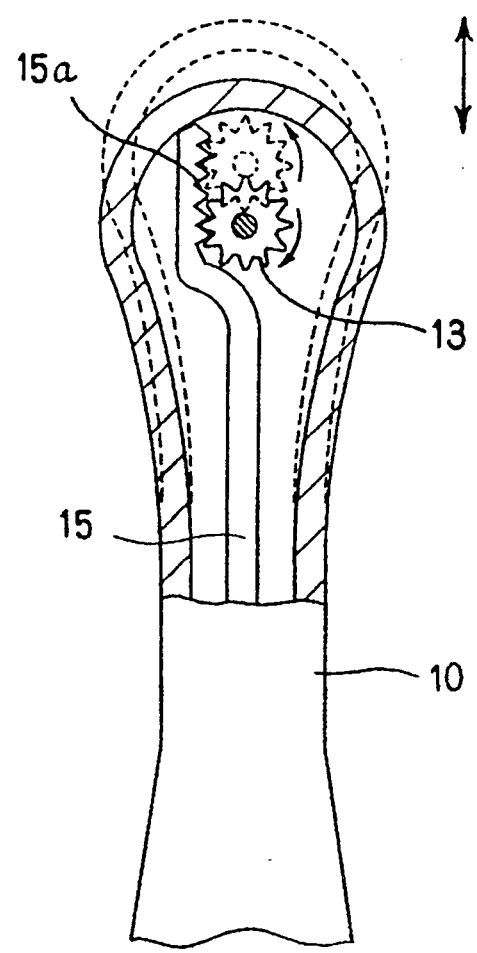
FIG. 3 is an enlarged partial cross-sectional view showing the action of the second transmission mechanism of the embodiment of FIG. 1.

Thus, although the attachment 10 moves as one body with the drive shaft 8, reciprocally up-and-down with respect to the case 1, the extending bar 15, which is connected to the fixed shaft 9, remains stationary with respect to the case 1. As a result, as shown in FIG. 3, the pinion 13, which meshes with the rack 15a of the top end of the extending bar 15, reciprocally rotates about the shaft 12 along with the up-and-down motion of the attachment 10. The rotary motion of this pinion 13 is directly transmitted to the rotary brush member 11, and the rotary brush member 11 reciprocally rotates on the attachment 10. In this way a second transmission mechanism which converts the up-and-down (axial direction) reciprocating motion of the attachment into a rotary motion is formed by the pinion 13 and the rack 15a.

The operation of this power toothbrush will now be explained.

When the case 1 is held and a switch, not shown in the drawings, is switched on ON, the direct current motor 2 rotates. The rotation of the direct current motor 2 passes through the motor pinion 6 and the bevel gear 4 and is converted into a reciprocating motion in the direction of the length of the case 1 and transmitted to the drive shaft 8 by the eccentric cam 4a and the cam follower 7 which make up the first transmission mechanism, and the attachment 10 moves as one body with the drive shaft 8, reciprocating up-and-down with respect to the case 1. As the attachment 10 reciprocates up-and-down, the pinion 13, which meshes with the rack 15a of the top end of the extending bar 15 which is connected to the fixed shaft 9 which is fixed to the case 1, reciprocally rotates about the shaft 12 (see FIG. 3), and the rotary brush member 11 reciprocally rotates at the end of the attachment 10.

In this preferred embodiment the first transmission mechanism, for converting the rotation of the direct current motor 2 into a reciprocal motion, is made up of the eccentric cam 4a and the cam follower 7. However, this is not the only possible arrangement, and various other methods, such as a link mechanism or a slider mechanism, could alternatively be used. Also, although in this preferred embodiment the second transmission mechanism, for converting the up-and-down (axial direction) reciprocating motion of the attachment 10 into a rotary motion, is made up of the pinion 13 and the rack 15a, this is not the only possible arrangement, and various other methods, such as a link mechanism or a slider mechanism, could alternatively be used.

Figure 5:
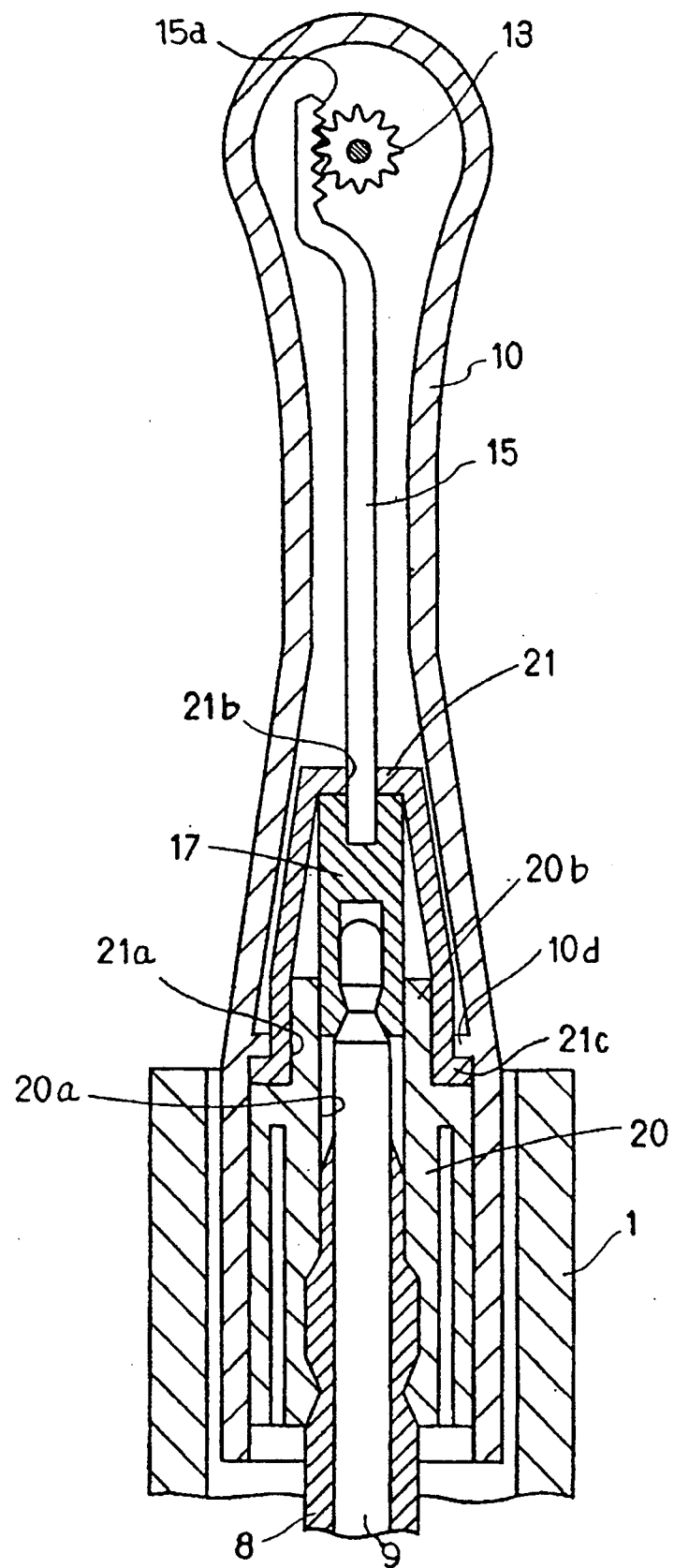
FIG. 5 is an enlarged cross-sectional view of the main parts of a second embodiment of the invention.

Next, a second preferred embodiment of the present invention will be described, with reference to FIG. 5.

In the preferred embodiment of FIG. 1, as shown in FIG. 4, it is conceivable that water entering through the gap between the attachment 10 and the rotary brush member 11 might pass between the drive shaft 8 and the fixed shaft 9 and get into the inner part of the case 1. The inner part of the case 1 contains such parts as the drive motor 2 and the dry cell battery (not shown in the drawings), and it is desirable that these parts do not get wet. In view of this, in a second preferred embodiment, as shown in FIG. 5, a cover 21 which covers the top end of the drive shaft 8 and the top end of the fixed shaft 9 is mounted inside the attachment 10. This cover 21 is hollow and generally cylindrical, has an opening 21a in the bottom, and has a through hole 21b, through which the extending bar 15 passes, in its top part. A flange 21c is provided around the perimeter of the bottom of the cover 21 and this flange 21c engages with an engaging protrusion 10d provided on the inside of the attachment 10. A protrusion 20b, formed so that it projects from the upper surface of the adaptor 20, engages with the inner wall surface of the cover 21. The inner surface of the protrusion 20b of the adaptor 20 is also the inner surface of the through hole 20a, and the bottom end of the coupler 17 fits into the protrusion 20b. The external diameter of the coupler 17 and the diameter (internal diameter) of the uppermost part of the interior of the cover 21 are equal, so that water entering through the gap between the attachment 10 and the rotary brush member 11 is prevented from passing through the through hole 21b and getting inside the cover 21.

If the top ends of the drive shaft 8 and the fixed shaft 9 are covered by the cover 21 in this way, water that has entered the attachment 10 is blocked off by the cover 21 and prevented from passing between the drive shaft 8 and the fixed shaft 9 and entering the inner part of the case 1.

As described above, in a power toothbrush according to the present invention, an attachment having a brush member is given a reciprocal motion and at the same time the brush member itself, mounted on the attachment, is given a rotary motion, so that a power toothbrush having an excellent brushing effect can have a simple construction and be made at low cost.

Also, if the top ends of the drive shaft and the fixed shaft are covered by a cover, water which has entered inside the attachment can be prevented from getting between the drive shaft and the fixed shaft, and the components housed inside the case can be prevented from getting wet.

What I claim is:

1. A power toothbrush comprising:
a case;
a drive motor operable to effect rotary motion mounted inside said case;
a drive shaft mounted inside said case in such a way that said drive shaft is free to move in an axial direction;
a first transmission mechanism for converting the rotary motion of said drive motor into a reciprocating motion and transmitting the reciprocating motion to said drive shaft;
an attachment carried by said drive shaft;
a rotary brush member mounted on said attachment; and
a second transmission mechanism for converting the reciprocating motion of said attachment in said axial direction into a rotary motion and transmitting this rotary motion to said rotary brush member.

2. A power toothbrush according to claim 1, wherein said second transmission mechanism comprises:
a fixed shaft inside said case;
an extending bar mounted inside the attachment in such a way that said attachment is free to move relative to said extending bar, said extending bar being connected to said fixed shaft;
a pinion provided on a shaft of said rotary brush member; and
a rack on said extending bar, said rack meshing with said pinion.

3. A power toothbrush according to claim 2, wherein said drive shaft has a hollow portion, said fixed shaft passes coaxially through said hollow portion of said drive shaft.

4. A power toothbrush according to claim 3, further comprising a cover mounted inside said attachment, said cover covering the end of said fixed shaft and said drive shaft.

5. A power toothbrush which simultaneously provides a reciprocatory and rotary brushing action comprising:
a case;
a power driven means in said case comprising a reciprocable drive member reciprocable relative to said case;
a rotary brush means carried by said drive member and reciprocable with said drive member;
an elongated member fixed to said case and extending to a position juxtaposed to said rotary brush means; and
operable means on said elongated member and on said rotary brush means operably engaged to effect rotation of said rotary brush means as said reciprocable drive member effects reciprocation of said rotary brush means, whereby said rotary brush means simultaneously provides a reciprocatory and rotary brushing action.

6. A power toothbrush according to claim 5, wherein said operable means comprises a rack and pinion gear, said pinion gear being on said rotary brush means, said rack being on said elongated member.

7. A power toothbrush according to claim 5, wherein said power driven means comprises a drive shaft, a rotary motor and transmission means for converting the rotary motion of said rotary motor to reciprocating motion of said drive shaft.

8. A power toothbrush according to claim 7, wherein said drive shaft has a hollow portion, said elongated member extending through said hollow portion of said drive shaft.

9. A power toothbrush according to claim 5, wherein said power driven means comprises an attachment means having a hollow portion which extends outside of said case, said elongated member extending through said hollow portion of said attachment means.

10. A power toothbrush according to claim 9, wherein said elongated member comprises a fixed shaft fixed to said casing, an extending bar, and connecting means connecting said fixed shaft to said extending bar, said connecting means being disposed in said hollow portion of said attachment means.

11. A power toothbrush according to claim 9, wherein said attachment means has one end on which said rotary brush means is mounted and another end on which an adaptor is mounted, said adaptor being fixed to said drive shaft, said adaptor having a through hole through which said elongated member passes.

* * * * *